(12) United States Patent
McMurtry et al.

(10) Patent No.: US 10,005,033 B2
(45) Date of Patent: Jun. 26, 2018

(54) ISOTOPIC ENRICHMENT OF HELIUM-3 THROUGH GLASS

(71) Applicants: Gary Michael McMurtry, Honolulu, HI (US); James Robert DeLuze, Honolulu, HI (US)

(72) Inventors: Gary Michael McMurtry, Honolulu, HI (US); James Robert DeLuze, Honolulu, HI (US)

(73) Assignees: Pacific Environment Technologies, LLC, Honolulu, HI (US); James Robert DeLuze, Honolulu, HI (US)

( * ) Notice: Subject to any disclaimer, the term of this patent is extended or adjusted under 35 U.S.C. 154(b) by 405 days.

(21) Appl. No.: 14/999,374

(22) Filed: Apr. 29, 2016

(65) Prior Publication Data
US 2016/0317971 A1  Nov. 3, 2016

Related U.S. Application Data

(60) Provisional application No. 62/179,193, filed on Apr. 29, 2015.

(51) Int. Cl.
*B01D 59/14* (2006.01)
*B01D 53/22* (2006.01)
(Continued)

(52) U.S. Cl.
CPC .............. *B01D 59/14* (2013.01); *B01D 53/30* (2013.01); *B01D 71/04* (2013.01);
(Continued)

(58) Field of Classification Search
CPC ...... B01D 53/228; B01D 53/30; B01D 59/12; B01D 59/14; B01D 71/04; C01B 23/0047;
(Continued)

(56) References Cited

U.S. PATENT DOCUMENTS 4,785,666 A * 11/1988 Bergquist .............. G01M 3/202
 62/55.5
5,545,894 A * 8/1996 Funsten ................. B01D 59/44
 250/281

(Continued)

OTHER PUBLICATIONS

Hauser, Andreas et al., "Nanoporous Graphene Membranes for Efficient 3He/4He Separation", Journal of Physical Chemistry Letters, 2012, 3, pp. 209-213. (Year: 2012).*

Primary Examiner — Jason M Greene

(57) ABSTRACT

Disclosed is a mass selective fluid bandpass filter. This filter provides for selecting gas molecules of a specific mass from a gas sample containing molecules of two or more mass species. This provides for a low power, low cost apparatus for producing $^3$He from terrestrial sources of helium gas by selective enrichment. This invention further discloses a portable, field deployable means of $^3$He/$^4$He ratio determination employing one or more of the effects consisting of: statistical linear regression plots of heat ramps, variable emission currents within a quadruple mass spectrometer, use of a quadrupole mass spectrometer in concert with ultrahigh vacuum maintained by non-evaporable getter pumps, and/or construction of vacuum housing structures from non-steel or non-stainless steel alloys, and or non metallic materials selected from a group consisting of: aluminum, titanium, ceramics, or glass. This provides a compact, sensitive field deployable unit with low power consumption.

21 Claims, 3 Drawing Sheets

(51) Int. Cl.
*B01D 53/30* (2006.01)
*B01D 71/04* (2006.01)
*H01J 49/00* (2006.01)
*H01J 49/42* (2006.01)
*C01B 23/00* (2006.01)
*G01N 33/00* (2006.01)
*H01J 49/04* (2006.01)

(52) U.S. Cl.
CPC ..... *C01B 23/0047* (2013.01); *G01N 33/0036* (2013.01); *B01D 53/228* (2013.01); *H01J 49/421* (2013.01); *H01J 49/4215* (2013.01)

(58) Field of Classification Search
CPC . G01N 33/0036; H01J 49/421; H01J 49/4215
See application file for complete search history.

(56) References Cited

U.S. PATENT DOCUMENTS

| | | | | |
|---|---|---|---|---|
| 6,231,642 B1* | 5/2001 | Shelby | ............... | B01D 53/22 95/45 |
| 2004/0149131 A1* | 8/2004 | Carboneri | ............ | B01D 53/228 96/4 |
| 2005/0247195 A1* | 11/2005 | Eriksen | ................ | B01D 59/12 95/82 |
| 2009/0173141 A1* | 7/2009 | Grosse Bley | ......... | G01M 3/205 73/25.05 |

* cited by examiner

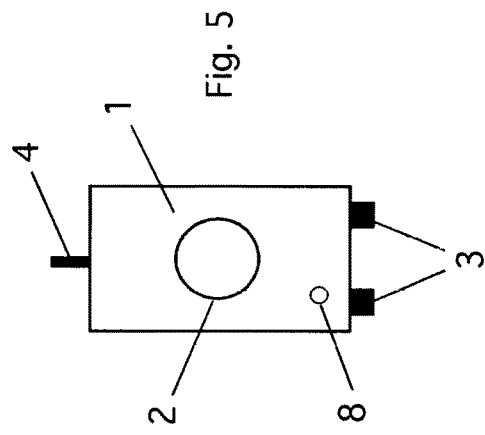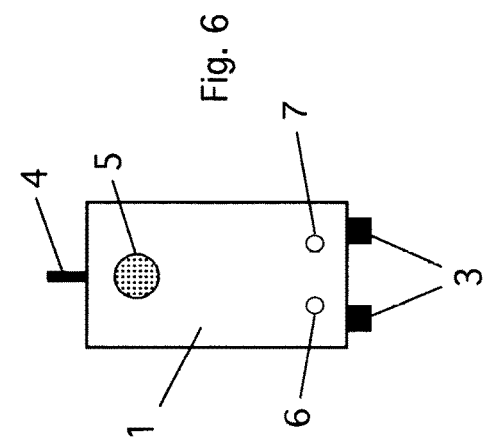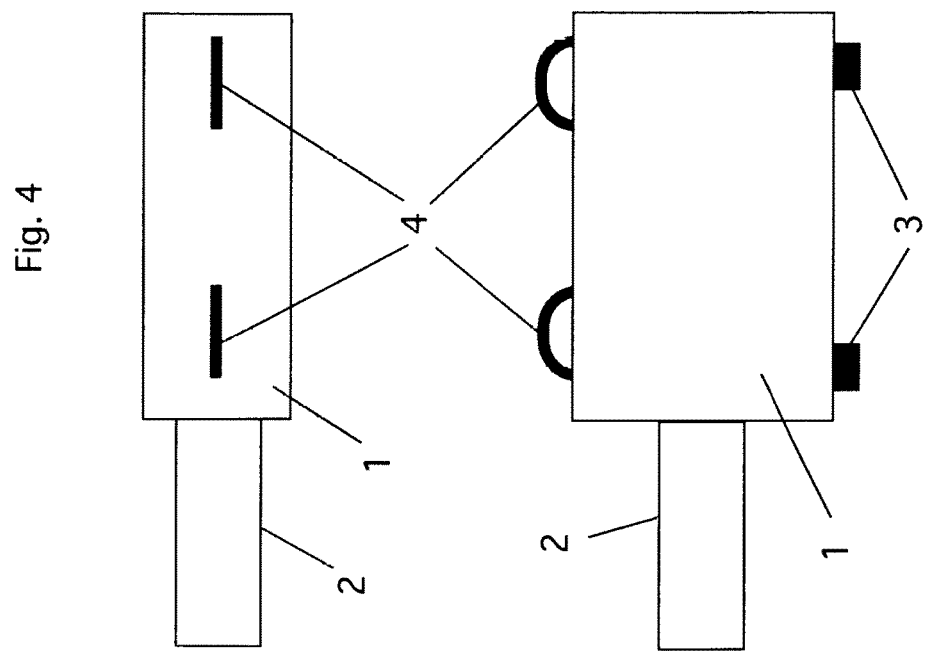

ISOTOPIC ENRICHMENT OF HELIUM-3 THROUGH GLASS

CROSS-REFERENCE TO RELATED APPLICATIONS

"This application claims the benefit of Provisional Patent Application Ser. No. 62/179,193, filed 2015 Apr. 29 by the present inventors."

FEDERALLY SPONSORED RESEARCH

Not applicable.

SEQUENCE LISTING OR PROGRAM

No listing.

BACKGROUND: FIELD OF INVENTION

Introduction $^3$He is a rare but important helium isotope. The lighter stable isotope of helium, $^3$He is primordial in the Earth, and is naturally created in space by spallation reactions of solar and cosmic rays with non-volatile particles. It is enriched in interplanetary dust and in the Moon's regolith by the latter process, and by direct accumulation of fusion products in the solar wind. $^3$He is enriched in Earth's mantle and deep mantle sources such as hot spot volcanism, and in the deep interiors of other planets such as Jupiter. Manmade sources include tritium decay from nuclear power reactors and tritium-fueled nuclear weapons. If $^3$He—$^3$He fusion could be achieved, which is widely considered a favorable nuclear reaction because of its high energy yield, negligible neutron radiation and ionized fusion products useful in electricity production (e.g., http://fti.neep.wisc.edu/neep602/lecture27.html, incorporated herein by reference), $^3$He would be valuable as a nuclear fuel, and suggestions to mine the Moon's regolith for its accumulated ppb-level content of $^3$He have been proposed (i.e., Fa, W.-Z. and Y-Q. Jin, 2010, Global inventory of Helium-3 in lunar regoliths estimated by a multi-channel microwave radiometer on the Chang-E 1 lunar satellite, Chinese Science Bull., 55, 4005-4009, incorporated herein by reference). More mundane uses include target material for neutron detectors used for laboratory fusion and related experiments and as portable nuclear security monitors. Because of the current and projected scarcity of helium reserves, concerns over the availability of $^3$He led the US Department of Homeland Security to propose in 2012 the conversion to alternative targets such as $^{10}$B (http://en.wikipedia.org/wiki/Helium-3, incorporated herein by reference).

Diffusion of $^3$He in Glass.

Diffusion of helium isotopes through natural glass and silicate minerals is commonly thought to obey classical dynamic laws where the diffusion rate of the isotope follows the mass and size of the atom. For natural glasses studied from 25° to 600° C., Trull (Trull, T. W., 1989 Diffusion of Helium Isotopes in Silicate Glasses and Minerals: Implications for Petrogenesis and Geochronology, Ph. D. dissertation, Woods Hole Oceanographic Institution and Mass. Inst. Technology, Woods Hole, Mass., 399 pp., incorporated herein by reference) found the fractionation to be about 8% in favor of the lighter $^3$He isotope over $^4$He (expressed as measured diffusivity ratios, D $^3$He/D $^4$He=1.08±0.02). This ratio is about 7% lower than classical inverse-square root of mass calculations, which suggest a 15% fractionation in favor of $^3$He based upon mass differences (D $^3$He/D $^4$He=1.15). Trull suggested the lower effect was due to quantization of helium vibrational energies, and suggested D $^3$He/D $^4$He would approach 1.15 at higher temperatures approaching those of the melt. Trull also suggested the 1.08 ratio was not composition dependent, but studied only natural glasses. Besides with elevated temperature, helium diffusion in glasses increases exponentially with silica glass purity (Altemose, V. O., 1961, Helium diffusion through glass, J. Applied Physics, 32 (7), 1309-1316; Norton, F. J. 1953, Helium diffusion through glass. J. Am. Ceram. Soc. 36, 90-96.; Rogers et al. 1954, Diffusion coefficient, solubility, and permeability for helium in glass, J. Appl. Phys. 25, 868-875; doi: 10.1063/1.1721760, incorporated herein by reference), so studies with pure quartz or silica glass of either natural or manmade origin may yield differing results.

Experimental Methods.

We used a commercial rounded-end quartz glass cylinder of 2.5-inch outside diameter, 7.5 inches length with 2-mm wall thickness that was fused to lower-temperature Pyrex™ glass in turn fused with Kovar™ to a stainless steel Conflat™ flange of 4.5 inches diameter. Heating was done by commercial heat tape wrapped around an aluminum cylinder with drilled holes that surrounded the quartz glass cylinder. The entire apparatus was surrounded by another aluminum cylinder to contain the heat by re-radiation. We used a Variac™ brand variable autotransformer to conduct the heat ramps, which were set and monitored by thermocouple, thermistor and IR temperature sensors. We used non-evaporable getter (NEG) and ion pumps to achieve ultra-high vacuum (UHV) monitored with a MKS Granville-Phillips model 390 full-range pressure gauge and an ion pump. Helium and other gases from 1-150 amu (Daltons) were measured by a MKS Granville-Phillips model 835 autoresonant ion trap mass spectrometer and a MKS Spectra Microvision 2 quadrupole mass spectrometer specially modified to obtain high sensitivity analysis in stability region I over a mass range of 1 to 6 amu. We operated solely in analog mode; no ion counting equipment for sensitive digital mode operation was necessary for these experiments. The heat ramps ranged from 2 to 5 hours duration and the glass was exposed to approximately one m$^3$ of lab air with an assumed helium concentration of 5.2 ppm by volume. The special MKS Spectra Microvision 2 mass spectrometer used has a peak mass resolution of about 400 M/dM where M=mass number. It is therefore not high enough in resolution to separate $^3$He from interfering isobars such as HD or $^3$H that need at least 650 M/dM to be fully resolved. To achieve this separation, we used a mass-2 versus mass-3 trend plot from the heat ramp peak response in factory-calibrated units of Torr. Total cycle, and warm-up and cool-down subsets were plotted from the maximum heat ramp temperature, with approximately 80-240 data pairs generated per trend that were highly linearly correlated. Statistical errors of the intercept were commonly under 3% at one sigma. Positive zero-intercepts at mass-2 yield the $^3$He residual partial pressure, which usually is only observed on the cool-down trend, and not on the warm-up trend when the glass is too cool to admit significant $^3$He in the relatively short ramp to maximum temperature of 1-hour duration.

Another method used to achieve this separation was the use of variable emission current from the filament ionizer (i.e., Davies et al., 2014, Threshold ionization mass spectrometry (TIMS): a complementary quantitative technique to conventional mass resolved mass spectrometry, Vacuum 101, 416-422., incorporated herein by reference), which can be programmed by the Microvision 2, but this approach requires low hydrogen abundance in the vacuum to be effective as a correction to the combined $^3$He-HD peak. A third approach is use of high hydrogen pumping speed NEG pumps to eliminate all potentially interfering hydrogen isobars (HD and $^3$H) (i.e., Frattolillo, A., De Ninno, A. 2007, A powerful tool to quantitatively detect tiny amounts of $^4$He in a deuterium rich background for fusion research, IEEE 1-4244-1194-7/07.; Frattolillo et al., 2007, Quantitative detection of tiny amounts of helium isotopes in a hydrogen isotope atmosphere using a standard-resolution quadrupole mass spectrometer, J. Vac. Sci. Technol. A, 25, 75-89., incorporated herein by reference). Except under special circumstances, environmental tritium ($^3$H) is too low to be a significant contributor to the mass-3 peak and can be neglected. A forth method to minimize hydrogen in the UHV is replacement of as much of the standard steel and stainless steel vacuum housing materials as practicable with either custom or commercial vacuum housing materials known to produce low to negligible hydrogen outgassing, such as alloys of aluminum or titanium, and glass or ceramic materials that can withstand high temperature (>200° C.) heating.

Results.

Through careful studies of the heating of pure quartz glass from ambient temperatures of ca. 20° to up to 226° C. in laboratory air, we have discovered a temperature window ranging from about 180° to 220° C. where $^3$He fractionates from $^4$He at the known air ratio ($R_a$) of $1.4\times10^{-6}$ $^3$He/$^4$He to values in excess of 250 times that ratio. An inverse exponential relationship exists between the maximum temperature of the applied heat ramp and the calculated $R/R_a$ of the laboratory air. Above about 226° C., the enrichment continues to drop exponentially to values approaching the air ratio, as the diameter of the silicon-oxygen ring structure continues to expand and the number of expanded rings in the quartz glass increases. Support for this interpretation is given by the complete absence of $^{22}$Ne in a pure 10:1 mixed $^3$He—$^{22}$Ne spike gas that was subjected to the same heat ramp conditions as the lab air, with a maximum observed $R/R_a$ of $1.70\times10^6$. Bajo et al. (Bajo, K., et al., 2012, Construction of a newly designed small-size mass spectrometer for helium isotope analysis: toward the continuous monitoring of $^3$He/$^4$He ratios in natural fluids, Mass Spectrometry, 1, A0009., incorporated herein by reference) measured $^{20}$Ne in lab air in contact with quartz glass heated to 700° C. They also found no significant fractionation of the air $^3$He/$^4$He isotope ratio (Bajo et al., 2012,).

In concert with other, related work on $^3$He/$^4$He enrichment (Hauser, A. W., and P. Schwerdtfeger 2011, Nanoporous graphene membranes for efficient $^3$He/$^4$He separation, J. Phys. Chem. Lett., 3, 209-213.; Hauser et al., 2012, Helium tunneling through nitrogen-functionalized graphene pores: pressure- and temperature-driven approaches to isotope separation, J. Phys. Chem. C, 116, 10819-10827., incorporated herein by reference), we suggest herein that $^3$He is enriched in the quartz glass at a specific temperature window as a result of heretofore-undiscovered quantum tunneling effects (i.e., Razavy, Mohsen 2003, Quantum Theory of Tunneling, World Scientific, pp. 4, 462. ISBN 9812564888., incorporated herein by reference). These enrichments may extend to lower temperature than 180° C., but the rate of helium diffusion in glass slows exponentially with decreasing temperature, which makes experimental determinations with our lab apparatus more difficult and time consuming. Nevertheless, $^3$He/$^4$He trends with temperature from a mixed $^3$He—$^{22}$Ne spike gas under similar heat ramp experimental conditions suggest that the relative $^3$He enrichment will decrease at temperatures below 180° C.

The air enrichment of $R/R_a$ to 250 translates to a $^3$He/$^4$He of $3.5\times10^{-4}$ through the quartz glass. Studies of $^3$He/$^4$He enrichment in nitrogen-modified graphene sheet structures have predicted enrichments of up to 19 at temperatures of 10° K (−263° C.) (Hauser and Schwerdtfeger, 2011). The enrichment difference is approximately $10^4$ in favor of the graphene sheet, but considerable power is required to maintain temperatures near absolute zero, compared with modest heating of quartz glass held to under 226° C. Nevertheless, Hauser and Schwerdtfeger consider their calculated flux of $10^{-9}$ moles/cm$^2$ sec to be commercially viable (with multistage purification of terrestrial helium sources at low temperature, one m$^2$ could yield more than 3 g $^3$He per day).

Other helium flux enhancement considerations include thinning the quartz glass membrane from our initial experimental conditions and applying pressure to the gas in contact with the glass. Even if only linear effects can be achieved, thinning the glass from 2 to 0.5 mm and increasing the gas pressure from ambient (ca. 15 psi or 1 bar) to 150 psi (10 bars) would increase the helium diffusion by about 40 fold, to 1500 psi (100 bars), by about 400 fold. Thin quartz glass windows supported by either sintered quartz glass or metal in contact with a vacuum have been previously proposed for a high-pressure, underwater variant of a portable $^3$He/$^4$He detector disclosed in U.S. patent application 20140264012 by McMurtry (2014), incorporated herein by reference. These glass windows can be made very thin and able to withstand a high-pressure differential by high-temperature heating to fuse the glass covering over the supporting sintered material.

Increased surface area is another important variable in the diffusion magnitude, as may be increased gas flow rate, which could also boost the diffusion efficiency. For example, the commercial quartz glass cylinder used herein has a surface area of 58.88 in$^2$ (380 cm$^2$). If increased to one m$^2$, the flux would increase linearly by more than 26 fold. Combining the above flux enhancements would provide for $10^3$ to $10^4$ enrichments, approaching in absolute amounts of $^3$He that of the graphene sheet at one m$^2$ area. Multiple passes of this gas would further increase the $^3$He/$^4$He ratio.

Summary of Experimental Results

We report the discovery of a temperature region in pure quartz glass where $^3$He is enriched relative to $^4$He to values much beyond those predicted by classical mechanics. $^3$He is a rare but important isotope to nuclear physics applications. Others have proposed methods to extract $^3$He from extraterrestrial materials with high $^3$He/$^4$He enrichment or use of membrane isotopic separation schemes that require high power consumption to extract $^3$He from terrestrial sources. Our discovery leads to a comparatively low power pathway to enrich $^3$He from terrestrial sources through glass membranes of high silica purity within a temperature window from ca. 180° to 220° C. Besides comparatively low power, the method's present apparatus is compact and easily scalable to industrial size. Among the suggested improvements, a method to increase the gas pressure over the glass is proposed based upon a previous disclosure by McMurtry (2014). Also disclosed are details of various methods used to detect the $^3$He/$^4$He in target materials and to monitor its enrichment progress, which expand upon the previous disclosure by McMurtry (2014).

Figure 1:
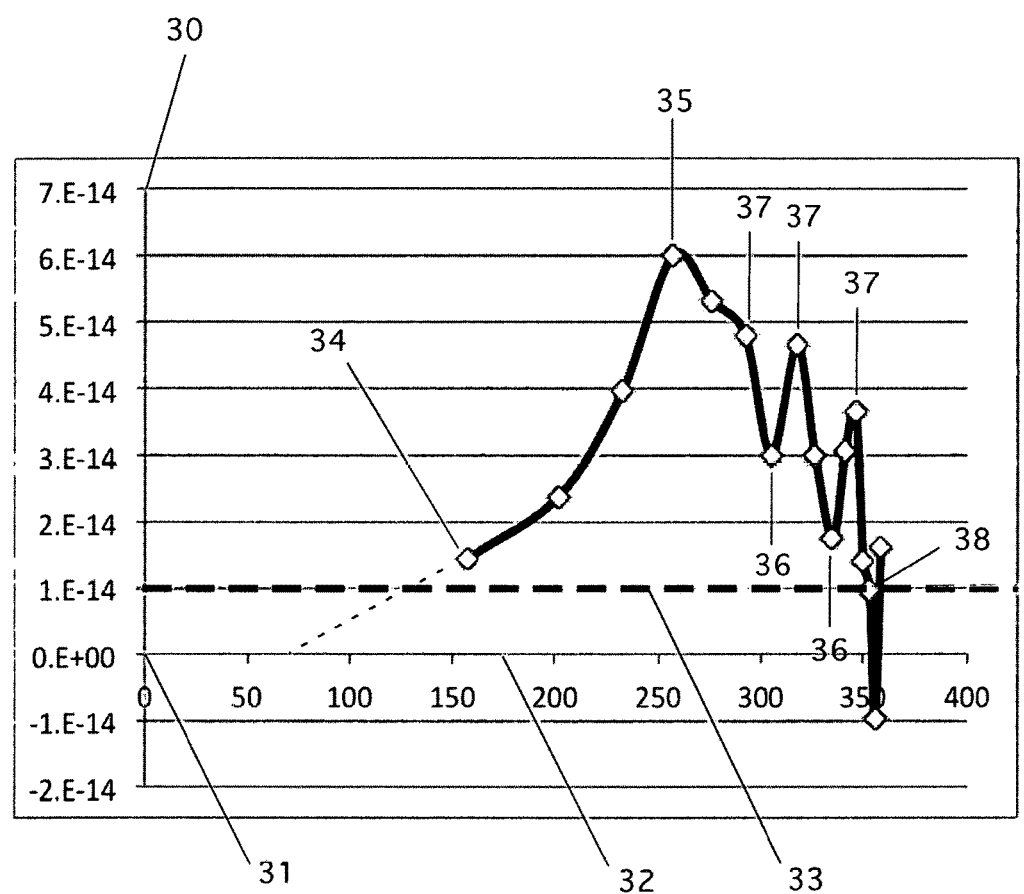
FIG. 1

A graph of a two-dimensional Cartesian coordinate system of ordered pairs where the ordinate, the y-axis, represents the partial pressure of $^3$He in Torr, and the abscissa, the x-axis, represent the temperature in degrees Celsius. This plot shows the relative opening and closing of ports allowing conductance of $^3$He at various temperatures in the upswing of a heat ramp.

FIG. 2

A see through representation of the components of the portable field deployable $^3$He/$^4$He ratio detector as seen from the left side.

FIG. 3

An outside view of the portable field deployable $^3$He/$^4$He ratio detector as seen from the left side.

FIG. 4

An outside view of the portable field deployable $^3$He/$^4$He ratio detector as seen from the top side.

FIG. 5

An outside view of the portable field deployable $^3$He/$^4$He ratio detector as seen from the front side.

FIG. 6

An outside view of the portable field deployable $^3$He/$^4$He ratio detector as seen from the back side.

REFERENCE NUMERALS IN DRAWINGS

1. $^3$He/$^4$He ratio detector case.
2. $^3$He/$^4$He ratio detector sample chamber.
3. Foot.
4. Handle.
5. Fan.
6. Power connector.
7. Communication connector.
8. Heater, thermocouple, and accessories power connector.
9. Quartz glass tube.
10. Graded glass seal.
11. Conflat adapter.
12. Sample chamber tube.
13. Sample chamber endcap.
14. Ultra high vacuum main chamber.
15. Conflat 90 degree elbow.
16. Conflat extension.
17. Flexible conflat extension.
18. Sample inlet pipe.
19. Sample outlet pipe.
20. Quadrupole mass spectrometer.
21. Non evaporable getter housing.
22. Non evaporable getter heater base with electrical connector.
23. Ion pump.
24. Autoresonant ion trap mass spectrometer.
25. In line electric conflat valve.
26. 90 degree electric conflat valve.
27. Cold cathode total pressure gauge.
28. Vacuum purge line with valves.
29. Electronics
30. Graph ordinate, the y-axis, representing $^3$He partial pressure in Torr.
31. Graph origin.
32. Graph abscissa, the X-axis, representing temperature in degrees Celsius.
33. Estimated noise floor of quadrupole mass spectrometer.
34. $^3$He gate opening point.
35. $^3$He gate closing point.
36. $^3$He high "Q" gate opening point.
37. $^3$He high "Q" gate closing point.
38. Point of $^3$He signal being swamped by other gases present.
39. Sample chamber enclosed space.
40. Ultra high vacuum enclosed space.

DESCRIPTION OF THE INVENTION

The method for determining the $^3$He/$^4$He ratio of a gas comprising $^3$He and $^4$He, provides for a portable and field deployable instrument, of a weight approximately 150 pounds, is able to be carried by approximately 2 to 4 persons, approximates 2 feet in width, approximates 3 feet in height, approximates 6 feet in length, consumes approximately 3 kilowatt hours per day, operates on electrical potential selected from a group consisting of 24 VDC, 120 VAC, 240 VAC and combinations thereof, and is enclosed in a weather resistant housing.

The essence of this invention are novel properties of quartz glass discovered by the inventors. It comprises a mass selective fluid bandpass filter. The mass selective fluid bandpass filter is a supercooled fluid. The supercooled fluid is quartz glass. The quartz glass wherein the quartz glass consists of quartz of either natural or manmade origin. The mass selective fluid bandpass filter of this apparatus provides for low-power operation. The mass selective fluid bandpass filter of this apparatus provides for a compact, field deployable unit. The mass selective fluid bandpass filter wherein this apparatus provides for a high sensitivity field deployable instrument for $^3$He/$^4$He ratio determination. The mass selective fluid bandpass filter provides a means for very selective filtering of gases of close atomic mass unit values within the operational range of this filter. The mass selective fluid bandpass wherein the specific atomic mass unit at which maximum transmission occurs is influenced by factors including temperature of the glass, differential pressure across the glass, and glass composition. The mass selective fluid bandpass wherein the atomic mass unit of maximum transmission has a direct relationship with the temperature of the glass. The mass selective fluid bandpass filter wherein this filter is a mass bandpass filter in that species of a given atomic mass unit under set conditions are selectively transmitted, whereas species of higher and lower atomic mass unit values are selectively blocked. The mass selective fluid bandpass filter wherein this filter exhibits a high quality, or Q characteristic. The mass selective fluid bandpass filter wherein with constant temperature operation, the filter can selectively pass species of a predetermined atomic mass unit value. The mass selective fluid bandpass filter wherein the sharp cutoff characteristics of this filter's transmission provides means for very selective filtering of gases of close atomic mass unit values within the operational range of this filter. The quartz glass is selectively semipermeable to the gases to to be filtered by this apparatus. The selective semipermeable action on the gases to to be filtered is based on conditions of glass thickness, glass temperature, glass composition, and pressure differential across the glass.

This mass selective filter provides a means of $^3$He/$^4$He ratio determination that is portable and field deployable and provides for a high sensitivity field deployable instrument for $^3$He/$^4$He ratio determination. The means of $^3$He/$^4$He ratio determination consists of a gas inlet and sample structure, a mass selective filter element, and a filtered gas outlet and analysis structure. The means of $^3$He/$^4$He ratio determination provides two internally bounded spaces which are separated by structures of stainless steel, borosilicate glass, sealing glass, and quartz glass. The structures of stainless steel, borosilicate glass, and sealing glass are impermeable to the gases to to be filtered by this apparatus. The quartz glass is selectively semipermeable to the gases to to be filtered by this apparatus. The selective semipermeable action on the gases to to be filtered described by the apparatus is based on conditions of glass thickness, glass temperature, glass composition, and pressure differential across the glass. The means of $^3$He/$^4$He ratio determination employs one or more of the effects selected from the group consisting of: 1) statistical linear regression plots of heat ramps, 2) variable emission current within a quadruple mass spectrometer, 3) use of a quadrupole mass spectrometer in concert with ultrahigh vacuum maintained by non evaporable getter pumps, 4) construction of vacuum housing structures from non-steel or non-stainless steel alloys, and or non metallic materials selected from a group consisting of: aluminum, titanium, ceramics, or glass, 5) or a mixture thereof. The statistical linear regression plots of heat ramps of provide for $^3$He/$^4$He ratio determination from statistical analysis of a mass-2 versus mass-3 trend plot from a heat ramp wherein determination of a positive zero-intercept of the y-axis of the mass-2 trend plot gives the $^3$He residual partial pressure. The variable emission current within a quadrupole mass spectrometer provide for $^3$He/$^4$He ratio determination wherein a predetermined programmed variation of emission current provides an effective correction to a combined $^3$He-HD peak when performed in a vacuum with low hydrogen abundance. The use of quadrupole mass spectrometer in concert with ultrahigh vacuum maintained by non-evaporable getter pumps provides for $^3$He/$^4$He ratio determination wherein the use of high hydrogen pumping speed non-evaporable getter pumps provides for the elimination of all potentially interfering hydrogen isobars of HD and $^3$H. The construction of vacuum housing structures from non-steel or non-stainless steel alloys, and or non metallic materials selected from a group consisting of: aluminum, titanium, ceramics, or glass provides for the $^3$He/$^4$He ratio determination wherein construction of vacuum housing structures is from materials known to produce low to negligible hydrogen outgassing, thereby minimizing the effect of all potentially interfering hydrogen isobars of HD and $^3$H.

The method for determining the $^3$He/$^4$He ratio of a gas comprising $^3$He and $^4$He, wherein the construction of vacuum housing structures from non-steel or non-stainless steel alloys, aluminum, titanium, and or non metallic materials selected from a group consisting of: ceramics, borosilicate glass, or sealing glass provides for vacuum housing structures that are impermeable to the gases to to be filtered by this apparatus. This construction of vacuum housing structures from non-steel or non-stainless steel alloys, aluminum, titanium, and or non metallic materials selected from a group consisting of: ceramics, borosilicate glass, or sealing glass provides for vacuum housing structures from materials known to produce low to negligible hydrogen outgassing, thereby minimizing the effect of all potentially interfering hydrogen isobars of HD and $^3$H.

FIG. 1 shows a portion of the initial up ramp of a heat ramp wherein the gates passing $^3$He selectively open prior to the gates passing $^4$He. The graph ordinate (30), the y-axis, represents $^3$He partial pressure in Torr. The graph origin is at (31). The graph abscissa (32), the X-axis, represents temperature in degrees Celsius. The estimated noise floor of quadrupole mass spectrometer is at (33). The sample points are approximately spaced by 1 minute. (34) shows a point in time wherein $^3$He gate opening point has been passed and $^3$He is entering the ultra high vacuum space (UHV). (35) indicates a $^3$He gate closing point, for though the temperature continues to rise, the $^3$He partial pressure starts to decline. (37) indicates a $^3$He high "Q" gate closing point, for the rate of decline in $^3$He partial pressure drops much more steeply. This is followed by a $^3$He high "Q" gate opening point at (36) wherein the $^3$He partial pressure increases very steeply. This is sequentially followed by several subsequent $^3$He high "Q" gate closing and opening points, ending with a final $^3$He high "Q" gate closing point and the $^3$He signal being swamped by other gases present at point (38). The area under this curve represents the $^3$He gas accumulation during this heat up ramp phase. After this time other gates open selectively passing 4He.

The high "Q" bandpass filter whose characteristics are shown in FIG. 1 as described above forms the core of a field deployable instrument capable of the $^3$He/$^4$He ratio in sample gases. Helium in general is 5.2 parts per million in regular air. Within this helium fraction, the $^3$He component normally is about one part per million, with the rest being $^4$He. That makes the $^3$He fraction one part per trillion in regular air. This would require a detector with over twelve orders of range to see $^3$He. The best quadrupole mass spectrometers may have a dynamic range of eight orders of range, but such instruments would not have the resolution see the difference between HD, $^3$He, and or $^3$H. Only large, expensive, heavy, lab equipment can make such determinations. Presently, sample gases are collected in copper tubes that are latter sent to labs for analysis. No field equipment exists for such determination. The importance is that $^3$He is primordial, and the $^3$He/$^4$He ratio significantly increases when magma is actively moving underground, as is common before earthquakes.

Figure 2:
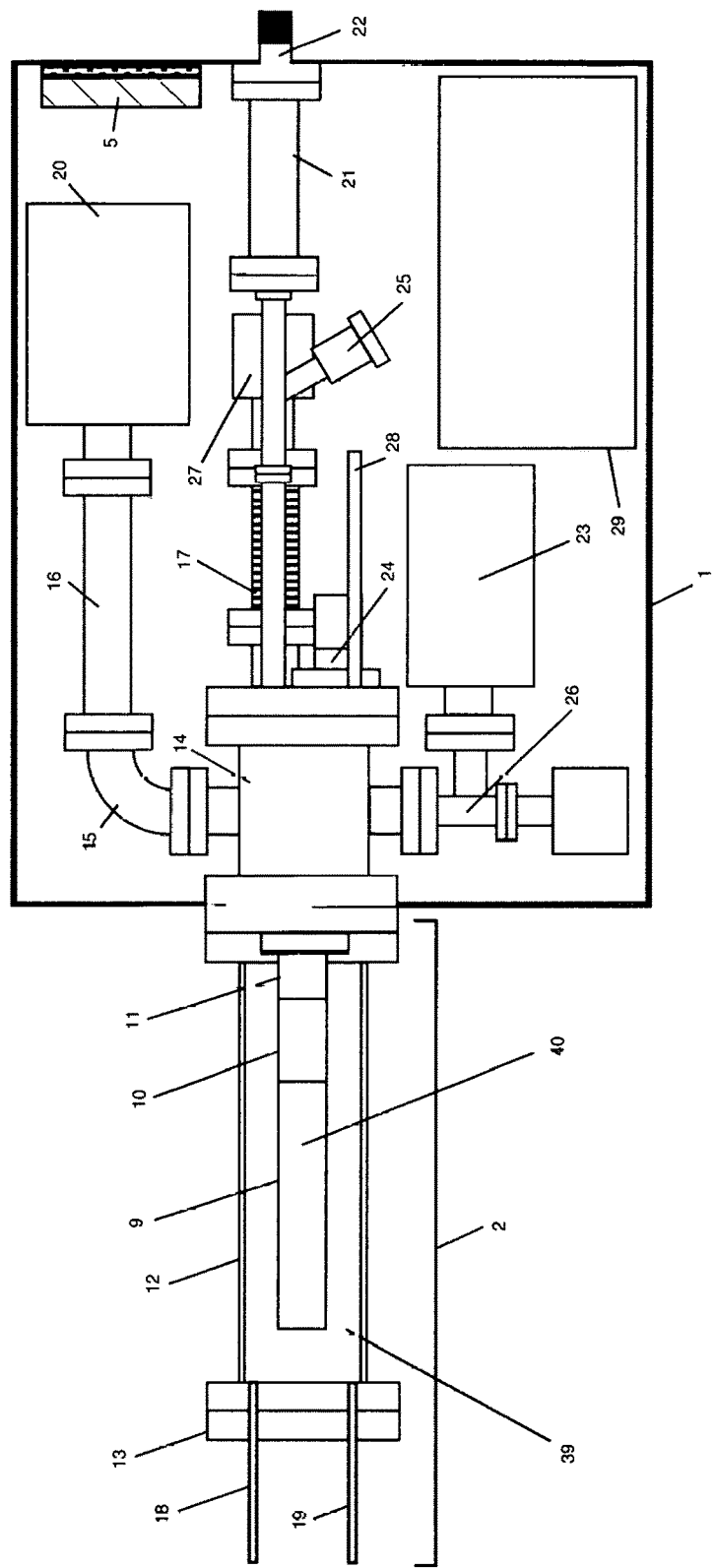

FIG. 2 shows a see through view of the field deployable instrument capable of the $^3$He/$^4$He ratio determination. Basically there are two separated, sealed spaces; the sample chamber enclosed space (39) separated from the ultra high vacuum enclosed space (40). The only communication between the two are microscopic gates which open and close, as controlled by temperature, in the quartz glass tube (9). This tube is connected to a conflat adapter (11) by a graded glass seal (10). Pieces (9), (10), and (11) are fused into one assembly, with the inner portion being continuous with the ultra high vacuum enclosed space (40). The outer portion is continuous with the sample chamber enclosed space (39).

The sample chamber enclosed space is the space bound by the Conflat adapter, the sample chamber tube (12), the sample chamber endcap (13), and the fused assembly of pieces (9), (10), and (11). Also shown are a sample inlet pipe (18), sample outlet pipe (19). For clarity, the electrical connections passing through the sample chamber endcap (13) are not shown.

The ultra high vacuum enclosed space is the internal volumes combined by the fused assembly of pieces (9), (10), and (11); the ultra high vacuum main chamber (14); the Conflat 90 degree elbows (15); the Conflat extension(s) (16); the flexible conflat extension (17); the quadrupole mass spectrometer (20); the autoresonant ion trap mass spectrometer (24); the exposed portion of the closed in line electric conflat valve (25); the exposed portion of the closed 90 degree electric conflat valve (26); the cold cathode total pressure gauge (27); and the vacuum purge line with valves (28) to the exposed portion of it's first closed valve.

The sample chamber enclosed space and the ultra high vacuum enclosed space have been found to be of nearly equal volumes in the units so far tested. In line electric conflat valve is connected to the non-evaporable getter housing (21) which is sealed of by its non-evaporable getter heater base with electrical connector (22).

The 90 degree electric conflat valve (26) is connected to the ion pump (23). When the electric conflat valves are open, the volume of the ultra high vacuum enclosed space is increased in volume by the enclosed spaces of these valves and their respective components. The same is true with the vacuum purge line and it's valves. However, it is the function of these units to rapidly pump out the gases contained within the ultra high vacuum enclosed space in preparation for another sample run.

In sampling and analysis mode, all of these valves are closed. The only entrance of gases into the ultra high vacuum enclosed space would be through open microscopic gates in the active region of the quartz glass tube.

The parts of this assembly are enclosed in the $^3$He/$^4$He ratio detector case (1). Within this case is an electronics assembly (29) to control all operation and then calculate and report the results. The sample chamber, sample chamber endcap, quartz glass tube with it's fused graded glass seal which is also fused to the conflat adapter, the sample inlet and outlet pipes, and all enclosed material are collectively referred to as $^3$He/$^4$He ratio detector sample chamber (2). Not shown for clarity are the heater windings on the quartz glass tube, the thermocouple above these windings, and the electrical connections. These parts are assembled in accordance with the standard procedures of those experienced with such art.

FIGS. 3, 4, 5, and 6 show external views of the unit. Included are individual foot(s) (3); handle(s) (4); a fan (5); a power connector (6); a communications connector (7); and a heater, thermocouple, and accessories power connector (8).

What is disclosed is a mass selective fluid bandpass filter. This filter provides for selecting gas molecules of a specific mass from a gas sample containing molecules of two or more mass species. This filter provides a means of operation of a portable, field deployable means of $^3$He/$^4$He ratio determination.

The mass selective bandpass filter consists of a gas inlet and sample structure, a mass selective filter element, and a filtered gas outlet and analysis structure. The filter element is a supercooled fluid consisting of quartz glass. The quartz glass of the filter element consists of quartz of either natural or manmade origin.

The gas inlet structure consists of a stainless steel tube with a Conflat™ flange at each end. The inlet end of the cylinder is sealed by a Conflat™ plate bolted to the flange and sealed with a copper gasket. Centered externally on this inlet plate is machined a smaller Conflat™ fitting and internal communicating passage to which a smaller Conflat™ plate is externally bolted and sealed with a copper gasket. Four high vacuum electrical connections pass through this smaller Conflat™ plate providing for internal electrical connections. Two stainless steel tubes pass through the larger Conflat™ which are attached at it's internal surface with high vacuum welds according to current practice of those experienced in such art.

The mass selective filter consists of a rounded-end quartz glass cylinder of 2.5-inch outside diameter, 7.5-inches length with 2-mm wall thickness. The open end of this cylinder is attached to a 2.5-inch borosilicate glass cylinder by a graded glass seal of sufficient layers of sealing glass to provide for adequate matching of the thermal expansion characteristics of the quartz cylinder to that of the borosilicate cylinder. This graded glass seal is fabricated according to current practice of those experienced in such art. The other open end of the borosilicate glass cylinder is attached to a 2.5-inch outside stainless steel cylinder according to current practice of those experienced in such art. The other open end of this stainless steel cylinder is vacuum welded to a 4.5-inch Conflat™ flange according to current practice of those experienced in such art.

The quartz glass section of the glass cylinder is wrapped with commercial heat tape whose electrical connections are attached to corresponding electrical connections passing externally through the smaller Conflat™ plate. A thermocouple or thermistor temperature sensor is attached to the heated portion of the quartz cylinder according to current practice of those experienced in such art. The electrical connections for the thermocouple or thermistor are attached to remaining two electrical connections passing externally through the smaller Conflat™ plate. These connections provide for external electrical connections to provide power for the heater and sensor readings for the cylinder temperature.

The 4.5-inch Conflat™ flange attached to the glass cylinder is bolted and sealed with a copper gasket to a machined Conflat™ fitting on the filtered gas outlet and collection structure. Peripherally and axially centered on this 4.5 inch machined Conflat™ fitting is machined a second Conflat™ fitting which matches the second Conflat™ flange on the stainless tube of the inlet structure. This second Conflat™ flange of the inlet structure is bolted and sealed with a copper gasket to the outer, second Conflat™ fitting machined on the filtered gas outlet and collection structure.

These components and structures are assembled according to current practice of those experienced in such art. This assemblage provides two vacuum tight external connections to an internally contained gas inlet structure space. This space is bounded by the internal surface of the gas inlet structure cylinder, the internal surface of the attached Conflat™ plate at the inlet end, the surface of the filtered gas outlet and collection structure in communication with said internal space, the external surfaces of the rounded-end quartz glass cylinder, the borosilicate glass cylinder, the graded glass seal, and the portion of the 4.5-inch Conflat™ flange in communication with this internal space.

This assemblage also provides a second internally contained space in communication with the gas analysis structures. This space is bounded by the internal surfaces of the rounded-end quartz glass cylinder, the borosilicate glass cylinder, the graded glass seal, and the portion of the 4.5-inch Conflat™ flange in communication with this second internal space.

This assemblage provides two internally bounded spaces which are separated by structures of stainless steel, borosilicate glass, sealing glass, and quartz glass. The stainless steel, borosilicate glass, and sealing glass are impermeable to the gases to to be filtered by this apparatus. The quartz glass is selectively semipermeable to the gases to to be filtered by this apparatus. The selective semipermeable action on the gases to to be filtered is based on conditions of glass thickness, glass temperature, glass composition, and pressure differential across the glass.

Gas comprising species of differing atomic and molecular mass is introduced through one of the stainless steel tubes. This sample gas may be circulated through the sample space by allowing sample gas to bleed out through the second stainless steel tube as determined by ancillary apparatus operated according to current practice of those experienced in such art.

Predetermined mass species from this gas mixture selectively are transmitted across the semipermeable quartz glass section of the mass selective filter. This outlet gas, concentrated to a given mass species exits through the filtered gas outlet to the gas analysis structures.

The semipermeable quartz glass filter behaves analogous to an electrical series resonant circuit comprised of resistance, capacitance, and inductance. Gas transmission is highest at the equivalent of series resonance wherein capacitive and inductive reactances cancel and circuit transmission is limited by the direct current (DC) resistance of the circuit. In this case, resonance represents the species molecular or atomic mass in Atomic Mass Units (AMU).

The specific AMU at which maximum transmission occurs is influenced by factors including temperature of the glass, differential pressure across the glass, and glass composition. It has been observed that AMU of maximum transmission has a direct relationship with the temperature of the glass. We have observed a positive correlation between AMU and glass temperature within the temperature ranges observed with our experiments. With increasing temperature, a higher value of AMU is selectively passed.

This filter is a mass bandpass filter in that species of a given AMU under set conditions are selectively transmitted, whereas species of higher and lower AMU values are selectively blocked. This filter exhibits a high quality, or Q, characteristic. Q is defined as relative transmission at a given AMU value compared with the rejection characteristic of species of slightly higher or lower values of AMU.

For a given set of operating characteristics of glass composition and differential pressure, the AMU value selectively passed is controlled by the temperature of the glass. Ancillary electronic apparatus determine this glass temperature and keep it within a predetermined temperature range by regulating the electric power supplied to the heater.

With constant temperature operation, the filter can selectively pass species of a predetermined AMU. Observed selectivity characteristics indicate that species within 1 AMU of its range can be selectively transmitted or rejected. The given species transmitted at a given time can be changed by adjusting the glass temperature.

The inverse exponential relationship found between the maximum temperature of the applied heat ramp and the calculated $R/R_a$ of the laboratory air indicates greater selective transmission of $^3$He than that of $^4$He, for the differential pressure of $^3$He across the glass is about 5 orders of magnitude lower than that of $^4$He. This is further suggestive that as the heat ramp temperature further increased, that this selective transmission of $^3$He then was decreased and at higher temperature selective passage $^4$He then occurred at these higher temperatures. The exponential drop of this curve was indicative of increasing transmission of $^4$He which had a partial pressure differential of about 6 orders of magnitude greater across the glass than that of the $^3$He. This sharp cutoff characteristic of the $^3$He transmission provides means for very selective filtering of gases of close AMU values within the operational range of this filter.

This invention provides means of $^3$He/$^4$He ratio determination which employs one or more of the effects selected from the group consisting of: 1) statistical linear regression plots of heat ramps, 2) variable emission current within a quadrupole mass spectrometer, 3) use of a quadrupole mass spectrometer in concert with ultrahigh vacuum maintained by non evaporable getter pumps, 4) construction of vacuum housing structures from non-steel or non-stainless steel alloys, and or non metallic materials selected from a group consisting of: aluminum, titanium, ceramics, or glass, 5) or a mixture thereof.

The statistical linear regression plots of heat ramps provides for $^3$He/$^4$He ratio determination from statistical analysis of a mass-2 versus mass-3 trend plot from a heat ramp wherein determination of a positive zero-intercept of the y-axis of the mass-2 trend plot gives the $^3$He residual partial pressure.

The variable emission current within a quadrupole mass spectrometer provides for $^3$He/$^4$He ratio determination wherein a predetermined programmed variation of emission current provides an effective correction to a combined $^3$He-HD peak when performed in a vacuum with low hydrogen abundance.

Operation of the Invention

What is disclosed is a method for determining the $^3$He/$^4$He ratio of a gas. This provides for selecting gas molecules of a specific mass from a gas sample containing molecules of two or more mass species. This method provides a means of operation of a portable, field deployable means of 3He/4He ratio determination.

A method for determining the $^3$He/$^4$He ratio of a gas comprising $^3$He and $^4$He comprising the steps of: providing a sample chamber, providing a mass selective supra cooled liquid bandpass filter in communication with the sample chamber, wherein the mass selective supra cooled liquid bandpass filter is made of quartz glass, introducing a sample of the gas comprising $^3$He and 4He into the sample chamber, heating the mass selective supra cooled liquid bandpass filter made of quartz glass, wherein the heating is performed as a heat ramp including through a temperature window of about 50 to 450° C., and allowing $^3$He and $^4$He to selectively pass through the mass selective supra cooled liquid bandpass filter from the sample chamber into an analysis structure during the heat ramp, wherein the analysis structure analyzes the partial pressures of $^3$He and $^4$He passing through the mass selective supra cooled liquid bandpass filter during the heat ramp to determine the $^3$He/$^4$He ratio.

The analysis structure determines the $^3$He/$^4$He ratio by statistical linear regression plots of heat ramps from statistical analysis of mass-2 versus mass-3 trend plot from a heat ramp wherein determination of a positive zero-intercept of the y-axis of the mass-3 plot gives the $^3$He residual partial pressure. The analysis structure additionally determines the $^3$He/$^4$He ratio with a variable emission current within a quadrupole mass spectrometer, wherein a predetermined programmed variation of emission current provides an effective correction to a combined $^3$He-HD peak when performed in a vacuum with low hydrogen abundance. The analysis structure comprises a quadrupole mass spectrometer in concert with ultrahigh vacuum maintained by non-evaporable getter pumps and ion pumps, wherein the non-evaporable getter pumps and ion pumps eliminate potentially interfering hydrogen isobars of HD and 3H.

The method for determining the $^3$He/$^4$He ratio of a gas comprising $^3$He and $^4$He of, further comprising the step of providing a vacuum housing between the mass selective supra cooled liquid bandpass filter made of quartz glass, wherein the quartz glass is of either natural or manmade origin, and the analysis structure, wherein the vacuum housing is formed from a material selected from a group consisting of aluminum, titanium, stainless steel, ceramics, borosilicate glass, sealing glass and combinations thereof.

The method for determining the $^3$He/$^4$He ratio of a gas comprising $^3$He and $^4$He, wherein $^3$He is separated from $^4$He when the mass selective supra cooled liquid bandpass filter is within the general given temperature window of about 50 to 450° C., and within the specific given temperature window of about 100 to 450° C.

The method for determining the $^3$He/$^4$He ratio of a gas comprising $^3$He and $^4$He, wherein the supra cooled liquid bandpass filter made of quartz glass provides a method for very selective filtering of gases of close atomic mass unit values within the operational range of this filter. This supra cooled liquid bandpass filter made of quartz glass provides a method wherein the atomic mass unit of maximum transmission has a direct relationship with the temperature of the supra cooled liquid bandpass filter made of quartz, and the supra cooled liquid bandpass filter made of quartz glass provides a method wherein species of a given atomic mass unit under set conditions are selectively transmitted, whereas species of higher and lower atomic mass unit values are selectively blocked, wherein said mass selective fluid bandpass filter exhibits a high quality, or Q characteristic. The supra cooled liquid bandpass filter made of quartz glass provides a method that is selectively semipermeable to the gases to to be filtered by this apparatus. The supra cooled liquid bandpass filter made of quartz glass provides a method whereby with constant temperature operation, the filter can selectively pass species of a predetermined atomic mass unit value. The supra cooled liquid bandpass filter made of quartz glass provides a method for very selective filtering of gases of close atomic mass unit values within the operational range of this filter.

The method for determining the $^3$He/$^4$He ratio of a gas comprising $^3$He and $^4$He, wherein the specific atomic mass unit at which maximum transmission occurs is influenced by factors including temperature of the supra cooled liquid bandpass filter made of quartz glass, thickness of the supra cooled liquid bandpass filter made of quartz glass, differential pressure across the supra cooled liquid bandpass filter made of quartz glass, and the composition of the supra cooled liquid bandpass filter made of quartz glass.

The method for determining the $^3$He/$^4$He ratio of a gas comprising $^3$He and $^4$He of wherein the method of calculating $^3$He/$^4$He ratio comprising the steps of: sample gas is introduced into a cleared sample chamber at about atmospheric pressure, a heat ramp is started at a predetermined power level, early within the temperature up ramp gates selectively passing $^3$He open resulting in a $^3$He temperature curve, with further temperature rise the $^3$He partial pressure drops below the noise level of the quadrupole mass spectrometer due to the very small amount $^3$He being masked by the rising levels of $^4$He, for a predetermined duration the average area under the $^3$He curve is computed wherein this area becomes the representation of the $^3$He fraction of the $^3$He/$^4$He ratio and is recorded, with further increase in temperature large amounts of $^4$He enter the ultra high vacuum portion of the instrument, after a predetermined time, the power is cut off to the heater, and the quartz glass undergoes a cool down phase, where during this cool down phase $^4$He continues to move through the open $^4$He gates wherein a $^4$He temperature curve is produced, at points during this cool down curve some $^3$He again enters but is negligible with relation to the $^4$He fraction, for a predetermined duration the average area under the $^4$He curve is computed wherein this area becomes the representation of the $^4$He fraction of the $^3$He/$^4$He ratio and is recorded, the ratio of the $^3$He area to the $^4$He area is reported as the $^3$He/$^4$He ratio.

What is disclosed is a method of a sequence of operation for determining the $^3$He/$^4$He ratio of a gas. This provides for selecting gas molecules of a specific mass from a gas sample containing molecules of two or more mass species. This method provides a means of operation of a portable, field deployable means of $^3$He/$^4$He ratio determination.

The method for determining the $^3$He/$^4$He ratio of a gas comprising $^3$He and $^4$He wherein the method of calculating $^3$He/$^4$He ratio comprising the steps of the following operations: a sample is introduced into the sample chamber, the quartz glass filter is heated to a predetermined temperature, the heated quartz glass filter provides for exclusive diffusion of helium and hydrogen, with higher temperatures the heated quartz glass filter more preferentially diffuses helium, the hydrogen gas diffused into the high vacuum chamber is selectively pumped and sequestered by the non-evaporable getter pump, the heating of the quartz glass filter is stopped after a predetermined amount of time, cooling of the quartz glass filter below 45 degrees Celsius effectively closes the quartz glass filter to further hydrogen and helium diffusion, the mass spectrometer measures the helium 3 and helium 4 abundance, electronics calculates and records the helium 3 to helium 4 ratio, the ultra high vacuum valve opens and exposes the vacuum chamber to the noble diode ion pump, the noble diode ion pump pumps and sequesters the helium gas level to below a set threshold as measured by the ultra high vacuum total pressure gauge, the apparatus is now prepared to receive another sample, the process is repeated, in the event that the helium is not pumped by the noble diode ion pump to below the set threshold in a predetermined amount of time such an indication is recorded, if telemetry is available this indication of not reaching a predetermined helium threshold level is telemetered, the unit is then shut down.

Objects and Advantages

Accordingly, besides the objects and advantages of the selective fluid bandpass filter and means for $^3$He/$^4$He ratio determination described in our patent application, several objects and advantages of the present invention are:

(a) to provide for a field deployable instrument for $^3$He/$^4$He ratio determination.

(b) to provide for a compact deployable instrument for $^3$He/$^4$He ratio determination.

(c) to provide for a low power instrument for $^3$He/$^4$He ratio determination.

(d) to provide for a high resolution field deployable instrument for $^3$He/$^4$He ratio determination.

(e) to provide for a commercial means of separation of $^3$He from available terrestrial helium sources.

(f) to provide for a commercial means of fusion reactor fuel production.

(g) to provide for a commercial means of target material for neutron detectors used for fusion laboratory experiments.

(h) to provide for a commercial means of target material for neutron detectors used for non-fusion laboratory experiments.

(i) to provide for a commercial means of target material for neutron detectors used in portable nuclear security monitors.

CONCLUSION, RAMIFICATIONS, AND SCOPE

In the descriptions above, the reader has seen several embodiments of our mass selective fluid bandpass filter and means of portable, field deployable $^3$He/$^4$He ratio determination. There are differing applications for these apparatus and means. One example is a portable, field deployable instrument for $^3$He/$^4$He ratio determination. Another example is a commercial means of separation of $^3$He from available terrestrial helium sources. These very different applications make best use of differing embodiments of our mass selective fluid bandpass filter.

The operational embodiment of this invention is applicable to $^3$He/$^4$He ratio determination and commercial $^3$He production. The basic mechanism of the mass selective fluid bandpass filter is to provide for the selective transmission of a gas of specific mass across the filter and provide for the selective blockage of transmission of related gases of nearly identical mass to that of the selected gas. Furthermore, the mass selective fluid bandpass filter and means of this invention has the additional advantages in that:

(a) the gas mass selected for transmission is controlled by the temperature of the filter.
(b) gases of nearby lower mass are selectively rejected.
(c) gases of nearby higher mass are selectively rejected
(d) the gas mass selected for transmission is adjustable by changing the temperature of the filter.
(e) to provide for a field deployable instrument for $^3$He/$^4$He ratio determination.
(f) to provide for a compact deployable instrument for $^3$He/$^4$He ratio determination.
(g) to provide for a low power instrument for $^3$He/$^4$He ratio determination.
(h) to provide for a high resolution field deployable instrument for $^3$He/$^4$He ratio determination.
(i) to provide for a high sensitivity field deployable instrument for $^3$He/$^4$He ratio determination.
(j) to provide for a commercial means of separation of $^3$He from available terrestrial helium sources.
(k) to provide for a commercial means of fusion reactor fuel production.
(l) to provide for a commercial means of target material for neutron detectors used for laboratory fusion experiments.
(m) to provide for a commercial means of target material for neutron detectors used for laboratory experiments.
(n) to provide for a commercial means of target material for neutron detectors used in portable nuclear security monitors.

While our above description contains many specificities, these should not be construed as limitations on the scope of the invention, but rather as an exemplification of one preferred embodiment thereof. Many other variations are possible. For example:

(a) thinning the quartz glass membrane from that of our initial experimental conditions.
(b) applying pressure to the gas in contact with the glass.
(c) increasing the pressure differential across the glass.
(d) using a multiplicity of tubes in the filter structure.
(e) supporting thin quartz glass windows by either sintered quartz glass or metal in contact with a vacuum.
(f) high-temperature heating to fuse the glass covering over the supporting sintered material.

In the descriptions above, we have put forth theories of operation that we believe to be correct. While we believe these theories to be correct, we don't wish to be bound by them. While there have been described above the principals of this invention in connection with specific apparatus, it is to be clearly understood that this description is made only by way of example and is not as a limitation to the scope of the invention. Accordingly, the scope of the invention should be determined not by the embodiment (s) illustrated, but by the appended claims and their legal equivalents.

We claim:

1. A method for determining the $^3$He/$^4$He ratio of a gas comprising $^3$He and $^4$He comprising the steps of:
providing a sample chamber,
providing a mass selective supra cooled liquid bandpass filter in communication with the sample chamber,
wherein the mass selective supra cooled liquid bandpass filter is made of quartz glass,
introducing a sample of the gas comprising $^3$He and $^4$He into the sample chamber,
heating the mass selective supra cooled liquid bandpass filter made of quartz glass, wherein the heating is performed as a heat ramp including through a temperature window of about 50 to 450° C.,
and allowing $^3$He and $^4$He to selectively pass through the mass selective supra cooled liquid bandpass filter from the sample chamber into an analysis structure during the heat ramp,
wherein the analysis structure analyzes the volumes of $^3$He and $^4$He passing through the mass selective supra cooled liquid bandpass filter during the heat ramp to determine the $^3$He/$^4$He ratio.

2. The method for determining the $^3$He/$^4$He ratio of a gas comprising $^3$He and $^4$He of claim 1, wherein the analysis structure determines the $^3$He/$^4$He ratio by statistical linear regression plots of heat ramps from statistical analysis of mass-2 versus mass-3 trend plot from a heat ramp wherein determination of a positive zero-intercept of the y-axis of the mass-3 plot gives the $^3$He residual partial pressure.

3. The method for determining the $^3$He/$^4$He ratio of a gas comprising $^3$He and $^4$He of claim 1, wherein the analysis structure determines the $^3$He/$^4$He ratio with a variable emission current within a quadrupole mass spectrometer, wherein a predetermined programmed variation of emission current provides an effective correction to a combined $^3$He-HD peak when performed in a vacuum with low hydrogen abundance.

4. The method for determining the $^3$He/$^4$He ratio of a gas comprising $^3$He and $^4$He of claim 1, wherein the analysis structure comprises a quadrupole mass spectrometer in concert with ultrahigh vacuum maintained by non-evaporable getter pumps and ion pumps.

5. The method for determining the $^3$He/$^4$He ratio of a gas comprising $^3$He and $^4$He of claim 1, wherein the non-evaporable getter pumps and ion pumps eliminate potentially interfering hydrogen isobars of HD and 3H.

6. The method for determining the $^3$He/$^4$He ratio of a gas comprising $^3$He and $^4$He of claim 1, further comprising the step of providing a vacuum housing between the mass selective supra cooled liquid bandpass filter made of quartz glass and the analysis structure, wherein the vacuum housing is formed from a material selected from a group consisting of aluminum, titanium, stainless steel, ceramics, borosilicate glass, sealing glass and combinations thereof.

7. The method for determining the $^3$He/$^4$He ratio of a gas comprising $^3$He and $^4$He of claim 1, wherein the quartz glass is of either natural or manmade origin.

8. The method for determining the $^3$He/$^4$He ratio of a gas comprising $^3$He and $^4$He of claim 1, wherein $^3$He is separated from $^4$He when the mass selective supra cooled liquid bandpass filter is within the general given temperature window of about 50 to 450° C.

9. The method for determining the $^3$He/$^4$He ratio of a gas comprising $^3$He and $^4$He of claim 1, wherein $^3$He is separated from $^4$He when the mass selective supra cooled liquid bandpass filter is within the specific given temperature window of about 100 to 450° C.

10. The method for determining the $^3$He/$^4$He ratio of a gas comprising $^3$He and $^4$He of claim 1, provides for a portable and field deployable instrument,
of a weight approximately 150 pounds,
is able to be carried by approximately 2 to 4 persons,
approximates 2 feet in width,
approximates 3 feet in height, approximates 6 feet in length, consumes approximately 3 kilowatt hours per day, operates on electrical potential selected from a group consisting of 24 VDC, 120 VAC, 240 VAC, and combinations thereof, and is enclosed in a weather resistant housing.

11. The method for determining the $^3$He/$^4$He ratio of a gas comprising $^3$He and $^4$He of claim 1, wherein the specific atomic mass unit at which maximum transmission occurs is influenced by factors including temperature of the supra cooled liquid bandpass filter made of quartz glass, thickness of the supra cooled liquid bandpass filter made of quartz glass, differential pressure across the supra cooled liquid bandpass filter made of quartz glass, and the composition of the supra cooled liquid bandpass filter made of quartz glass.

12. The method for determining the $^3$He/$^4$He ratio of a gas comprising $^3$He and $^4$He of claim 1, wherein the supra cooled liquid bandpass filter made of quartz glass provides a method for very selective filtering of gases of close atomic mass unit values within the operational range of this filter.

13. The method for determining the $^3$He/$^4$He ratio of a gas comprising $^3$He and $^4$He of claim 1, wherein the supra cooled liquid bandpass filter made of quartz glass provides a method wherein the atomic mass unit of maximum transmission has a direct relationship with the temperature of the supra cooled liquid bandpass filter made of quartz.

14. The method for determining the $^3$He/$^4$He ratio of a gas comprising $^3$He and $^4$He of claim 1, wherein the supra cooled liquid bandpass filter made of quartz glass provides a method wherein species of a given atomic mass unit under set conditions are selectively transmitted, whereas species of higher and lower atomic mass unit values are selectively blocked, wherein said mass selective fluid bandpass filter exhibits a high quality, or Q characteristic.

15. The method for determining the $^3$He/$^4$He ratio of a gas comprising $^3$He and $^4$He of claim 1, wherein the construction of vacuum housing structures from non-steel or non-stainless steel alloys, aluminum, titanium, and or non metallic materials selected from a group consisting of: ceramics, borosilicate glass, or sealing glass provides for vacuum housing structures that are impermeable to the gases to to be filtered by this apparatus.

16. The method for determining the $^3$He/$^4$He ratio of a gas comprising $^3$He and $^4$He of claim 1, wherein the supra cooled liquid bandpass filter made of quartz glass provides a method that is selectively semipermeable to the gases to to be filtered by this apparatus.

17. The method for determining the $^3$He/$^4$He ratio of a gas comprising $^3$He and $^4$He of claim 1, wherein the supra cooled liquid bandpass filter made of quartz glass provides a method whereby with constant temperature operation, the filter can selectively pass species of a predetermined atomic mass unit value.

18. The method for determining the $^3$He/$^4$He ratio of a gas comprising $^3$He and $^4$He of claim 1, wherein the supra cooled liquid bandpass filter made of quartz glass provides a method for very selective filtering of gases of close atomic mass unit values within the operational range of this filter.

19. The method for determining the $^3$He/$^4$He ratio of a gas comprising $^3$He and $^4$He of claim 1, wherein the construction of vacuum housing structures from non-steel or non-stainless steel alloys, aluminum, titanium, and or non metallic materials selected from a group consisting of: ceramics, borosilicate glass, or sealing glass provides for vacuum housing structures from materials known to produce low to negligible hydrogen outgassing, thereby minimizing the effect of all potentially interfering hydrogen isobars of HD and $^3$H.

20. The method for determining the $^3$He/$^4$He ratio of a gas comprising $^3$He and $^4$He of claim 1, wherein the method of calculating $^3$He/$^4$He ratio comprising the steps of:

sample gas is introduced into a cleared sample chamber at about atmospheric pressure, a heat ramp is started at a predetermined power level, early within the temperature up ramp gates selectively passing $^3$He open resulting in a $^3$He temperature curve, with further temperature rise the $^3$He partial pressure drops below the noise level of the quadrupole mass spectrometer due to the very small amount $^3$He being masked by the rising levels of $^4$He, for a predetermined duration the average area under the $^3$He curve is computed wherein this area becomes the representation of the $^3$He fraction of the $^3$He/$^4$He ratio and is recorded, with further increase in temperature large amounts of $^4$He enter the ultra high vacuum portion of the instrument, after a predetermined time, the power is cut off to the heater, and the quartz glass undergoes a cool down phase, where during this cool down phase $^4$He continues to move through the open $^4$He gates wherein a $^4$He temperature curve is produced, at points during this cool down curve some $^3$He again enters but is negligible with relation to the $^4$He fraction, for a predetermined duration the average area under the $^4$He curve is computed wherein this area becomes the representation of the $^4$He fraction of the $^3$He/$^4$He ratio and is recorded, the ratio of the $^3$He area to the $^4$He area is reported as the $^3$He/$^4$He ratio.

21. The method for determining the $^3$He/$^4$He ratio of a gas comprising $^3$He and $^4$He of claim 1, wherein the method of calculating $^3$He/$^4$He ratio comprising the steps of the following operations:

a sample is introduced into the sample chamber, the quartz glass filter is heated to a predetermined temperature, the heated quartz glass filter provides for exclusive diffusion of helium and hydrogen, with higher temperatures the heated quartz glass filter more preferentially diffuses helium, the hydrogen gas diffused into the high vacuum chamber is selectively pumped and sequestered by the non-evaporable getter pump, the heating of the quartz glass filter is stopped after a predetermined amount of time, cooling of the quartz glass filter below 45 degrees Celsius effectively closes the quartz glass filter to further hydrogen and helium diffusion, the mass spectrometer measures the helium 3 and helium 4 abundance, electronics calculates and records the helium 3 to helium 4 ratio, the ultra high vacuum valve opens and exposes the vacuum chamber to the noble diode ion pump, the noble diode ion pump pumps and sequesters the helium gas level to below a set threshold as measured by the ultra high vacuum total pressure gauge, the apparatus is now prepared to receive another sample, the process is repeated, in the event that the helium is not pumped by the noble diode ion pump to below the set threshold in a predetermined amount of time such an indication is recorded,
if telemetry is available this indication of not reaching a predetermined helium threshold level is telemetered,
the unit is then shut down.

* * * * *